March 12, 1963 G. MERRILL Plant Pat. 2,240
NECTARINE TREE
Filed Dec. 12, 1961
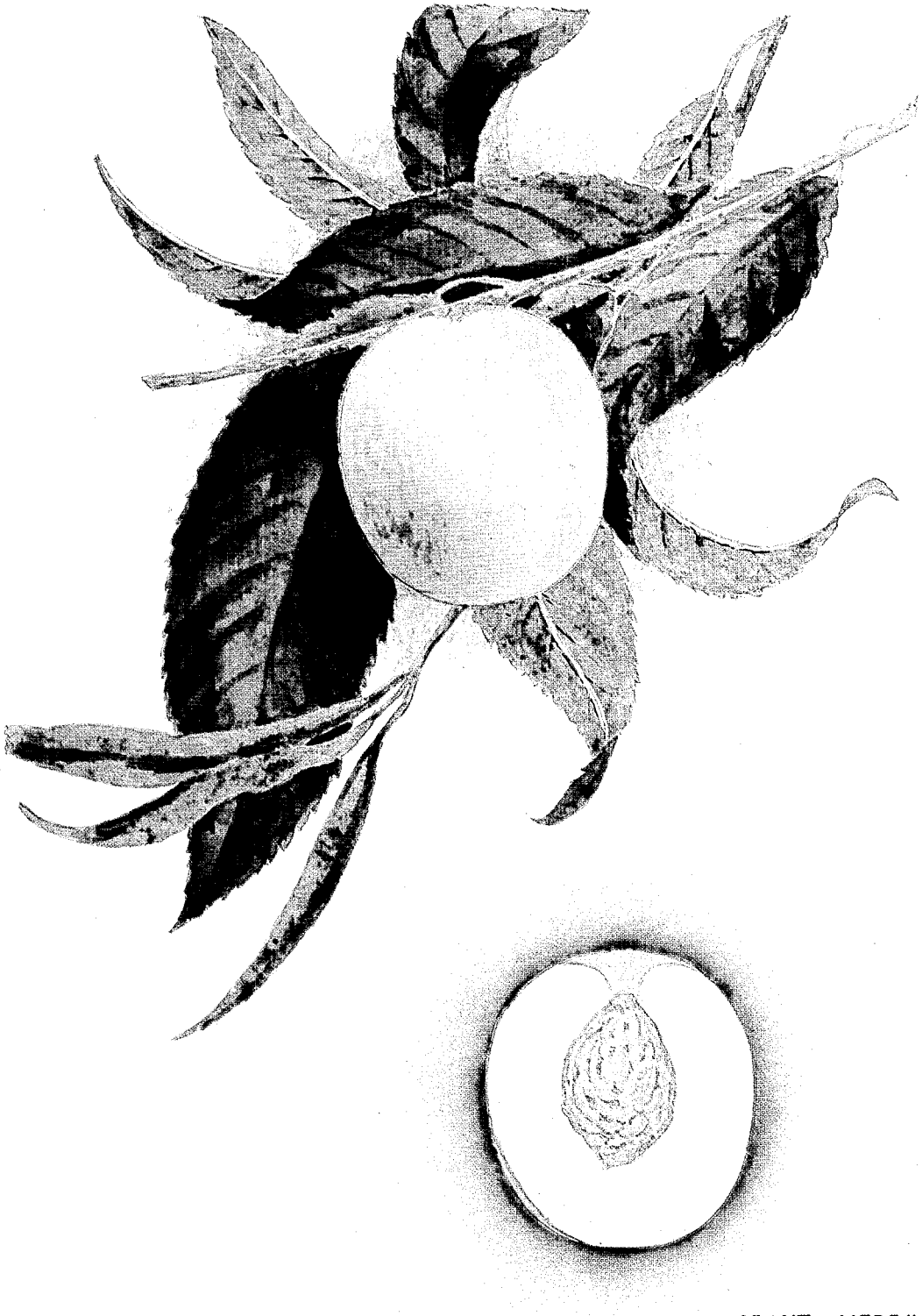
WITNESS
Addison I. Avery
INVENTOR
GRANT MERRILL
HUEBNER & WORREL
ATTORNEYS
BY Richard M. Worrel United States Patent Office Plant Pat. 2,240
Patented Mar. 12, 1963

2,240
NECTARINE TREE

Grant Merrill, P.O. Box 392, Red Bluff, Calif.

Filed Dec. 12, 1961, Ser. No. 158,919
1 Claim. (Cl. 47—62)

The present invention relates to a nectarine tree and more particularly to a new and distinct variety thereof, broadly characterized by being a strong vigorous tree which bears very early in the harvest seasons and produces firm, semi-freestone nectarines having a high content of soluble solids when firm ripe, with half to almost all of the skin colored a bright red.

The subject variety most nearly resembles Merrill Sunrise nectarine (P.P. No. 1,256), but is an improvement thereover in its ripening three to ten days earlier with a brighter red skin color and with fewer russet-like speckles. On the average, it ripens about one week earlier than the Sunrise nectarine.

The rich soil and favorable climatic environment prevailing in most of the commercial nectarine farming areas of California causes a tendency in nectarine trees to produce rank growth and dense shade. This results in serious impairment of the coloring of the fruit. Inasmuch as most fruits rely on eye appeal for their sales, color impairment is a substantial commercial handicap and is highly undesirable. A primary object of the plant breeding procedures which resulted in the development of this new nectarine variety was to achieve a highly colored red nectarine fruit which would maintain its color even under conditions of rank growth and dense shade.

A collateral object was to produce a new variety of nectarine tree characterized by moderate but consistent fruit set which minimized pruning and thinning requirement without being subject to irregular production.

Further objects and advantages will become apparent in the subsequent description in the specification.

In the drawing which is a water color painting, the upper portion shows a characteristic twig of the subject nectarine tree having leaves and a mature fruit thereon, the skin thereof having a heavy red blush over most of its surface, and the characteristic long shape of the fruit also being shown. The lower portion shows a characteristic fruit divided along its suture plane to illustrate the color of the flesh and the seed and to show the typically, partly free stone.

The most distinctive characteristics in the instant variety of nectarine tree are its early ripening, its brilliant red skin coloring, its long shape and its high soluble solids content when firm ripe.

This new variety of nectarine was produced by me on my farm near Red Bluff, Tehama County, California as an open pollinated embryo cultured seedling of Merrill Sunrise (P.P. No. 1,256). The present variety was asexually propagated by budding onto a seedling tree in our virus isolation plot at Corning, Tehama County, California, in 1958. When this budded tree came into bearing in 1960, fruit and other characteristics of this nectarine proved to be identical with the original nectarine tree.

Referring more specifically to the pomological characteristics of this new and distinct variety of nectarine tree, the following have been observed under the ecological conditions prevailing at my farm near Red Bluff, Tehama County, California and is an outline description thereof. All major color plate indentifications are by reference to Maerz and Paul Dictionary of Color.

*Tree*

Shape: large size, vigorous, medium upright, medium dense, vase shaped by pruning, productive and regular bearer.

Trunk: Medium slender, medium shaggy, dull grey, lenticels numerous.

Branches: Medium shaggy, dull grey on older branches, grey-brown on the younger branches, lenticels numerous and medium size.

Leaves: (selected from midportion of vigorous unbranched terminal shoots 12″ to 18″ long):

*Size.*—Medium.
*Length.*—5½″ to 7″, average 6⅜″.
*Width.*—1¼″ to 1⅞″, average 1 7/16″.
*Form.*—Lanceolute, tip acuminate.
*Thickness.*—Medium.
*Color.*—Upper surface medium green (22–L–6); undersurface lighter yellow-green (21–L–6); heavy under midrib much lighter and yellower green (18–J–1).
*Class.*—(Meader and Blake: Proceedings Am. Soc. Hor. Sc., vol. 37, page 206).—Class 2. Width-length ratio.—.22 average. Apex angle (1″ from tip)—30° to 40°, average 35° Base angle (½″ from petiole)—80° to 90°, average 83°.
*Margin.*—Crenate.
*Petiole.*—Medium length, medium slender.
*Stipules.*—At base of leaf, falling off early.
*Glands.*—None to 5, average 2 to 3, mostly alternate, small, reniform, color, green, turning to reddish brown later in season; position, on petiole and at base of leaf.

Flower buds: Medium size, plump, free, pubescent.

Flowers: Midseason to late bloom, approximately in season with Merrill Sunrise (Plant Patent No. 1,256). Large, showy, pink color.

*Anthers.*—Yellow with some orange.
*Pollen.*—Abundant.

*Fruit*

Maturity when described—firm ripe.

Size: Variable.

*Axial diameter.*—2¼″ to 2¾″, average 2½″.
*Transverse in suture plane.*—2 1/16″ to 2½″, average 2 3/16″.
*At right angles to suture plane (cheek to cheek).*—2⅛″ to 2½″, average 2 5/16″.

Form: Oblong, some fruits globose.

*Suture.*—An inconspicious shallow line, and slightly marked depression beyond pistil point on some.
*Ventral surface.*—Rounded throughout, lips unequal.
*Cavity.*—Rounded, elongated in suture plane.
*Base.*—Truncate.
*Apex.*—Rounded, pistil point apical when present.
*Stem.*—Length ⅛″ to 3/16″; diameter about ⅛″.
*Skin.*—Medium thick, medium tender, tenacious to flesh. Tendency to crack—slight. Color—under color, orange yellow (9–L–7), to (3–K–11) with red blush (4–L–6).

Flesh:

*Color.*—In lightest areas (9–K–5) to darker orange (9–H–9). Some mottling in flesh of ripe fruit.
*Amygdalin.*—Moderate.
*Juice.*—Abundant.
*Texture.*—Firm.
*Fibers.*—Few and fine.
*Ripens.*—Evenly to slightly earlier on the apical end.
*Flavor.*—Mild.
*Aroma.*—Distinct.
*Eating quality.*—Good.

Stone: Cling when hard ripe, sometimes almost completely freestone when soft ripe.

*Fibers.*—Short.

*Size.*—Length 1 1/16" to 1 3/8", average 1 1/8"; breadth 7/8" to 1 1/8", average 1"; thickness, 3/4" to 1", average 15/16".

*Form.*—Elliptical, with distinct apical tip.

*Base.*—Usually oblique.

*Hilum.*—Oval.

*Apex.*—Acuminate.

*Sides.*—Equal, flattened on either side.

*Surface.*—Irregularly furrowed and pitted throughout; pits circular to elongated.

*Ventral edge.*—Thick without wing.

*Dorsal edge.*—Narrow with deep groove on some, less deep on others.

*Color.*—Very light tan when dry.

Use: Good for fresh market whether local or distant. Acceptable for canning.

Shipping quality: Good.

Having thus described my new nectarine tree, what is claimed as new and desired to be secured by Letters Patent is:

A new and distanct variety of nectarine tree substantially as illustrated and described, characterized by its strong, vigorous growth; by its bearing of firm, semi-freestone fruit having a high content of soluble solids when firm ripe and a skin of bright red color from approximately one-half to entire surface; and by its most nearly resembling Merrill Sunrise nectarine of Plant Patent No. 1,256 but being an improvement thereover in that its fruit has a brighter red skin color with fewer russet-like speckles and ripens three to ten days earlier.

No references cited.